(12) United States Patent
Durst et al.

(10) Patent No.: US 8,680,473 B2
(45) Date of Patent: Mar. 25, 2014

(54) MULTIPLY-SAMPLED CMOS SENSOR FOR X-RAY DIFFRACTION MEASUREMENTS WITH CORRECTIONS FOR NON-IDEAL SENSOR BEHAVIOR

(75) Inventors: Roger D Durst, Middleton, WI (US); Gregory A Wachter, Sun Prairie, WI (US); Joerg Kaercher, Madison, WI (US)

(73) Assignee: Bruker AXS, Inc., Madison, WI (US)

( * ) Notice: Subject to any disclaimer, the term of this patent is extended or adjusted under 35 U.S.C. 154(b) by 303 days.

(21) Appl. No.: 13/285,089

(22) Filed: Oct. 31, 2011

(65) Prior Publication Data

US 2013/0108021 A1    May 2, 2013

(51) Int. Cl.
*G01T 1/18*    (2006.01)

(52) U.S. Cl.
USPC .................................. 250/370.09; 250/252.1

(58) Field of Classification Search
USPC ...................................................... 250/370.09
See application file for complete search history.

(56) References Cited

U.S. PATENT DOCUMENTS

| | | | |
|---|---|---|---|
| 5,250,824 A | 10/1993 | Janesick | |
| 5,541,402 A | 7/1996 | Ackland | |
| 5,818,052 A * | 10/1998 | Elabd | 250/370.09 |
| 6,307,915 B1 | 10/2001 | Frojdh | |
| 6,927,796 B2 | 8/2005 | Liu | |
| 6,963,370 B2 | 11/2005 | DiCarlo | |
| 8,319,307 B1 * | 11/2012 | Williams | 257/461 |
| 2003/0098919 A1 | 5/2003 | Liu | |
| 2008/0083876 A1 * | 4/2008 | Endo et al. | 250/369 |
| 2010/0020933 A1 * | 1/2010 | Topfer et al. | 378/98.11 |

OTHER PUBLICATIONS

T. He, et al., A large area X-ray imager with online linearization and noise suppression, Proc. of SPIE, Aug. 21, 2011, pp. 1-8, vol. 8142.
L. Eklund, et al., First results from the HEPAPS4 active pixel sensor, Nuclear Instruments and Methods in Physics Research A, Jan. 1, 2009, pp. 64-66, vol. 598.
Fowler, A. M. and Gately, I, "Demonstration of an Algorithm for Read-Noise Reduction in Infrared Arrays", The Astrophysical Journal, v. 353, L33-L34 (1990).
Lim, S. and Abbas, E. G. "Gain Fixed Pattern Noise Correction via Optical Flow", Sensors and Camera Systems for Scientific, Industrial, and Digital Photography Applications III, Morley M. Blouke, John Canosa, Nitin Sampat, Editors, Proceedings of SPIE v. 4669, pp. 384-391 (2002).
Young, E. T., Scutero, M., Rieke, G. Milner, T., Low, F. J., Hubbard, P. and Davis, J. "Far-infrared Focal Plane Development for SIRTF", Infrared Readout Electronics, Proceedings of SPIE, v. 1684, pp. 63-74 (1992).
Kawai, N., Kawahito, S., and Tadokoro, Y., "A Low-noise Oversampling Signal Detection Technique for CMOS Image Sensors", Proceedings of IEEE Instrumentation and Measurement Technology Conference, Anchorage, Alaska, v. 1, pp. 256-268, (May 2002).

* cited by examiner

*Primary Examiner* — Marcus Taningco
(74) *Attorney, Agent, or Firm* — ROBIC, LLP

(57) ABSTRACT

Readout noise for each pixel in a CMOS Active Pixel Sensor is reduced by a five step process in which the pixel charge data from the sensor is non-destructively sampled at a plurality of times during a sensor frame time period and corrected for gain variation and nonlinearity. Then fixed pattern and dark current noise is estimated and subtracted from the corrected pixel charge data. Next, reset noise is estimated and subtracted from the pixel charge data. In step four, a model function of charge versus time is fit to the corrected pixel charge data samples. Finally, the fitted model function is evaluated at frame boundary times.

22 Claims, 4 Drawing Sheets

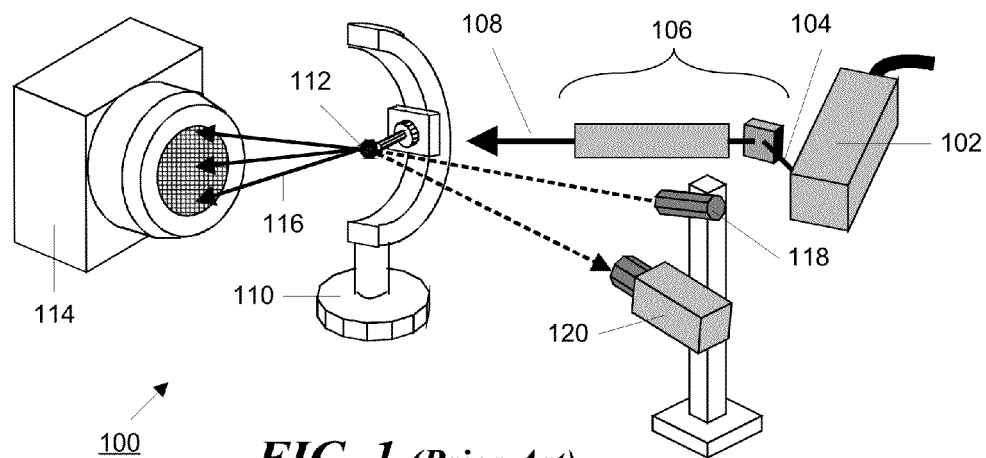
FIG. 1 *(Prior Art)*
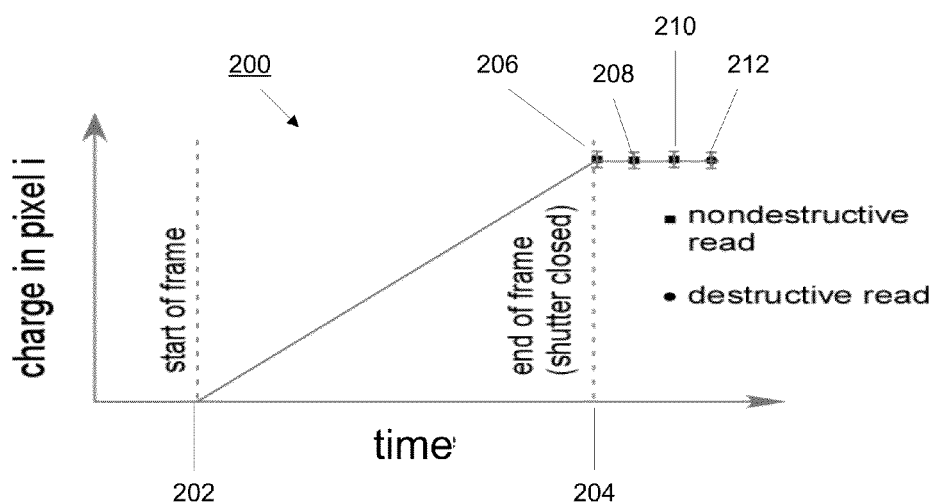
FIG. 2 *(Prior Art)*

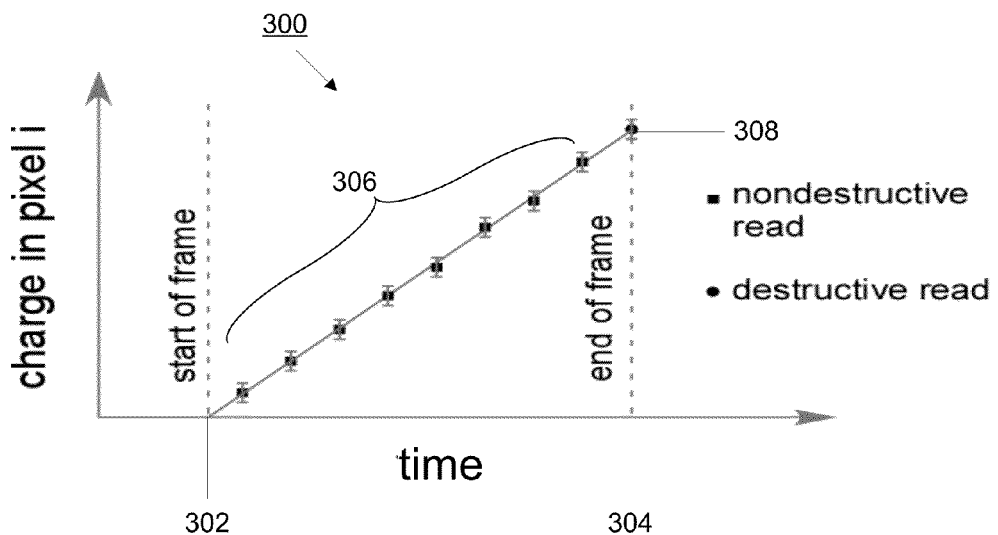
FIG. 3 *(Prior Art)*
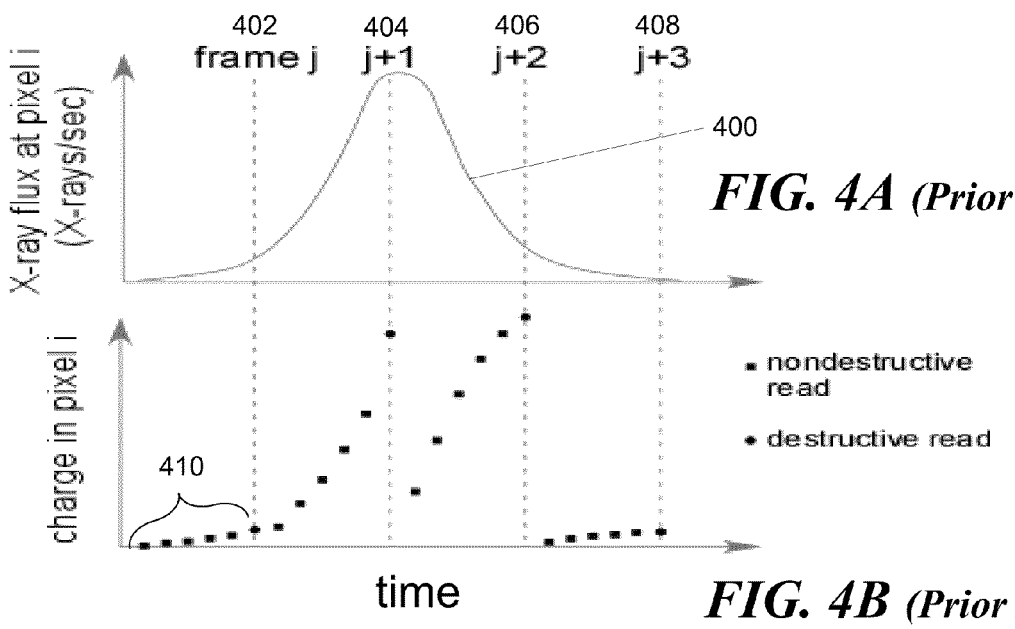
FIG. 4A *(Prior Art)*
FIG. 4B *(Prior Art)*

MULTIPLY-SAMPLED CMOS SENSOR FOR X-RAY DIFFRACTION MEASUREMENTS WITH CORRECTIONS FOR NON-IDEAL SENSOR BEHAVIOR

BACKGROUND

This invention relates to X-ray diffraction systems. X-ray diffraction is a non-destructive technique for the qualitative and quantitative analysis of crystalline material samples, which are generally provided in the form of single crystals. In accordance with this technique, an X-ray beam is generated by an X-ray tube with a stationary anode, by a conventional rotating anode X-ray source or by a synchrotron source and directed toward the material sample under investigation. When the X-rays strike the sample, they are diffracted according to the atomic structure of the sample.

A typical laboratory system 100 for performing single crystal diffraction experiments normally consists of five components as shown in FIG. 1. The components include an X-ray source 102 that produces a primary X-ray beam 104 with the required radiation energy, focal spot size and intensity. X-ray optics 106 are provided to condition the primary X-ray beam 104 to a conditioned, or incident, beam 108 with the required wavelength, beam focus size, beam profile and divergence. A goniometer 110 is used to establish and manipulate geometric relationships between the incident X-ray beam 108, the crystal sample 112 and the X-ray sensor 114. The incident X-ray beam 108 strikes the crystal sample 112 and produces scattered X-rays 116 which are recorded in the sensor 114. A sample alignment and monitor assembly comprises a sample illuminator 118, typically a laser, that illuminates the sample 112 and a sample monitor 120, typically a video camera, which generates a video image of the sample to assist users in positioning the sample in the instrument center and monitoring the sample state and position.

The goniometer 110 allows the crystal sample 112 to be rotated around several axes. Precise crystallography requires that the sample crystal 112 be aligned to the center of the goniometer 110 and maintained in that center when rotated around the goniometer rotational axes during data collection. During exposure, the sample (a single crystal of the compound of interest) is rotated in the X-ray beam 108 through a precise angular range with a precise angular velocity. The purpose of this rotation is to predictably bring Bragg angle reflections from each atomic plane of the sample into resonance with the incident beam 108 for the same period of time. During this time, called the charge integration time, the pixels of the sensor receive and integrate the X-ray signals.

Current generation X-ray area sensors 114 used for crystallography, include charge coupled devices (CCDs), Image Plates and CMOS sensors. CMOS Active Pixel Sensors (APS) have a number of advantages compared to CCD detectors for applications in X-ray detection. The advantages include high speed readout, high quantum gain and large active areas. However, the readout noise (comprised primarily of thermal noise on capacitors, commonly called kTC noise, 1/f noise and dark current shot noise) of these devices is typically about an order of magnitude larger than the readout noise of CCDs.

One conventional method for reducing the effective readout noise in CMOS sensors is to oversample the charge stored in the pixel sites. More specifically, many CMOS APS devices can be read out non-destructively which means the charge in a given pixel may be sampled multiple times without resetting the value of the charge. An article entitled "Demonstration of an Algorithm for Read-Noise Reduction in Infrared Arrays", A. M. Fowler and Ian Gatley, *The Astrophysical Journal*, 353:L33-L34, (1990) describes a technique in which an array is readout non-destructively N times after charge integration as shown schematically in FIG. 1 in order to reduce noise.

FIG. 2 is a schematic diagram 200 showing the charge in a pixel i on the vertical axis versus time on the horizontal axis. At the frame start time 202, the charge in the pixel is zero. The charge then linearly increases during the frame exposure time until the end of the frame at time 204 at which time a shutter is closed in order to prevent further X-rays from charging the pixel. Then, in this example, three non-destructive reads, 206, 208 and 210 are performed. Finally, a destructive read 212 is performed in order to reset the charge in the pixel to zero in preparation for the next exposure.

Theoretically, by observing the same random variable N times, the noise can be reduced by a factor of $$\frac{1}{\sqrt{N}}.$$

In the aforementioned article, Fowler et al showed experimentally that the effective noise is reduced by a factor very close to this theoretically expected factor. The same technique is also described for a specialized CCD with a non-destructive readout capability in U.S. Pat. No. 5,250,824. However, reducing noise in this manner has the obvious disadvantage that the readout dead time is increased by a factor of N times the array readout time. For example, if the array is oversampled nine times then the readout noise is reduced by approximately $\sqrt{9}=3$ times but the total readout dead time is increased by nine times. In both prior art cases mentioned above, this technique was proposed primarily for astronomical observations where the increase in readout dead time was acceptable. However, for more dynamic applications this increase in readout dead time is most often unacceptable.

A different approach is described in an article entitled "Far-infrared focal plane development for SIRT", E. T. Young, M. Scutero, G. Rieke, T. Milner, F. J. Low, P. Hubbard, J. Davis, E. E. Haller, and J. Beeman, *Infrared Readout Electronics, Proceedings SPIE*, v. 1684, pp. 63-74. (April 1992). In accordance with this technique called "Multiple Sample Correlation", a CMOS pixel is sampled N times during charge integration (that is, while the sensor is being exposed to the X-rays). This sampling is shown schematically in FIG. 3, which is a schematic diagram 300 also showing the charge in a pixel i on the vertical axis versus time on the horizontal axis. At the frame start time 302, the charge in the pixel is zero. The charge then linearly increases during the frame exposure time until the end of the frame at time 304 at which time a shutter is closed in order to prevent further X-rays from charging the pixel. However, unlike the previous technique, in this example eight non-destructive reads 306 are made during the pixel integration time. A final destructive read 308 is made at the end of the frame time 304 to reset the pixel charge to zero in preparation for the next frame.

A similar technique was also described in an article entitled "A low-noise oversampling signal detection technique for CMOS image sensors", N. Kawai, S. Kawahito, and Y. Tadokoro, *Proceedings of IEEE Instrumentation and Measurement Technology Conference*, Anchorage, Ak., v. 1, pp. 256-268 (May 2002). In accordance with this latter technique, the output of a CMOS imager is sampled N times. The resultant signals are then fed back into the readout circuit through a D-to-A converter. This technique allows the same sort of $$\frac{1}{\sqrt{N}}$$

noise reduction as the previous technique without having to read the array out N times (thus reducing the external data rate).

While the general approach of using multiple non-destructive readouts to improve the noise or dynamic range performance of a sensor is well established, the prior art assumes that the illumination source is invariant with time or varies in a predictable fashion. In particular, the aforementioned prior art techniques that sample during integration implicitly assume that the scene being imaged is static. That is, the photon flux incident on each pixel is constant during the pixel integration time. Of course, this is not the case in an X-ray diffraction system in which the diffracted X-rays serve as the illumination source.

Also, the aforementioned prior art techniques that sample during integration assume that the sensor response is otherwise ideal. In particular, they assume that the sensor response is perfectly linear. However, in an actual CMOS sensor, the output is not linear but typically shows nonlinearities of a few percent. Therefore, a simple application of the prior art techniques will not reduce the noise in a CMOS sensor output due to the errors induced by the sensor nonlinearity. The prior art also neglects the contributions of dark current noise and fixed pattern noise.

It would be strongly desirable to reduce the noise of CMOS devices while preserving the other benefits.

SUMMARY

In accordance with the principles of the invention, readout noise in a CMOS Active Pixel Sensor is reduced by a five step process in which the pixel charge data from the sensor is first corrected for gain variation and nonlinearity. Then fixed pattern and dark current noise is estimated and subtracted from the corrected pixel charge data. Next, reset noise is estimated and subtracted from the pixel charge data. In step four, a model function of charge versus time is fit to the corrected pixel charge data. Finally, the fitted model function is evaluated at frame boundary times.

In one embodiment, pixel charge data is first corrected for gain variation and nonlinearity by measuring the output of each pixel in response to a large number of calibration images and fitting the pixel response to a curve. In another embodiment, the calibration images are flood field images.

In another embodiment, fixed pattern and dark current noise are estimated by measuring the output of each pixel in response to a large number of calibration images and averaging the output of each pixel over the number of calibration images. In still another embodiment, the calibration images are identical dark images.

In yet another embodiment, reset noise is estimated from each image by performing a spatial frequency filtration on the image to determine the component with zero spatial frequency in each row. In this process of frequency filtration, bright signals (such as Bragg reflections) are detected and masked out. Then, a fast Fourier transform is applied to the image followed by low pass filtration.

In still another embodiment, reset noise is estimated from each image by masking off a number of pixels at the edge of the sensor and averaging the signal in these pixels.

In another embodiment, an optimal estimate of the charge in each pixel at the read out time of each frame is calculated from multiple non-destructive measurements during the frame integration time period of the charge in that pixel corrected for gain variation, nonlinearity, fixed pattern noise, dark current noise and reset noise. In another embodiment the optimal estimate is calculated by fitting the corrected measurements to a basis function of time. In still another embodiment, the basis function is a cubic polynomial in time.

In yet another embodiment, an optimal estimate of the integrated X-ray fluence at a pixel is obtained by evaluating the fitted basis function at frame boundary times, summing the optimal estimate over adjacent frame times and then dividing the sum by the average conversion gain.

BRIEF DESCRIPTION OF THE DRAWINGS

FIG. 1 shows a schematic diagram of a conventional laboratory X-ray diffraction system.

FIG. 2 is a graph of showing stored charge in a pixel versus time in a system in which the charge is integrated over a frame time, a shutter is closed to shut off X-rays and then the stored charge in the pixel is read non-destructively.

FIG. 3 is a graph of showing stored charge in a pixel versus time in a system in which the stored charge in the pixel is read non-destructively during the frame integration time and then a further destructive read is performed at the end of the frame time.

FIG. 4A is a graph showing the X-ray flux at a pixel versus time of a sample taken over several frame time periods (a sample rocking curve).

FIG. 4B is a graph showing a set of frames where during each frame multiple samples of the accumulated charge at the pixel shown in FIG. 4A are acquired, then pixel is reset at the end of the frame.

DETAILED DESCRIPTION

In an X-ray diffraction experiment, a sample is typically rotated at a constant angular velocity while exposed to an X-ray beam in order to generate diffracted X-ray images. It is well known that a CMOS sensor can be directly exposed to the X-ray flux or coupled via a scintillator screen to record these diffracted X-ray images. FIG. 4A shows the typical diffracted X-ray flux at a particular pixel i on the sensor on the vertical axis versus time on the horizontal axis. It can be seen that the flux 400 increases with time as the rotation of the sample causes it to come into Bragg resonance with the incident X-ray beam and then decreases with time again as the sample passes through resonance. This signal pattern is typically called a "rocking curve" of the sample.

When the X-ray diffraction system operates in a so-called "narrow frame" or "fine slicing" mode, the time between frame readouts is typically selected to be small enough so that this rocking curve spans several adjacent frames as shown schematically in FIG. 4A where the frame start times (402, 404, 406 and 408) of frames j, j+1, j+2 and j+3 are indicted by dotted lines. During the time duration of each frame (called the frame "integration time") the incident X-rays cause charge to accumulate in a capacitor associated with pixel i. If multiple samples of this accumulated charge are acquired, then the signals (such as signals 410) shown in FIG. 4B are observed. Each signal represented by a dark square is simply the value of time integral of the charge in pixel i read non-destructively at the respective sampling time. At the beginning of a new frame integration time, the accumulated charge is reset to zero as indicated by the dark circle. The accumulated charge signal $q_i(t)$, which is sampled for pixel i at a sampling time t, is given for frame j ($t_j < t < t_{j+1}$):

$$q_i(t) = \int_{t_j}^{t} [(g(F_i(\tau) - F_i(t_j)) + i_{dark,i}] d\tau + n_{FPN,i} + n_{reset,i} + n_{read,i} \quad (1)$$

where $F_i$ is the incident X-ray flux on pixel i, $g_i$ is the quantum conversion gain of pixel i (that is, the conversion gain from X-rays to electrons), $i_{dark}$ i is the dark current associated with pixel i and $n_{FPN,i}$, $n_{reset,i}$ and $n_{read,i}$ are the primary noise sources associated with the pixel i, namely, the so called fixed pattern noise ($n_{FPN}$), the reset noise ($n_{reset}$) and the read noise ($n_{read}$) which includes the kTC noise of the pixels as well as noise introduced by the read electronics.

What is needed is an optimal estimate of the total fluence of X-rays at pixel i based on the series of measurements of the charge in pixel i measured over several frames as shown in FIG. 4B.

$$F_{tot} = \int_{t_j}^{t_{j+2}} (F(\tau) - F(t_j)) d\tau \quad (2)$$

Figure 5:
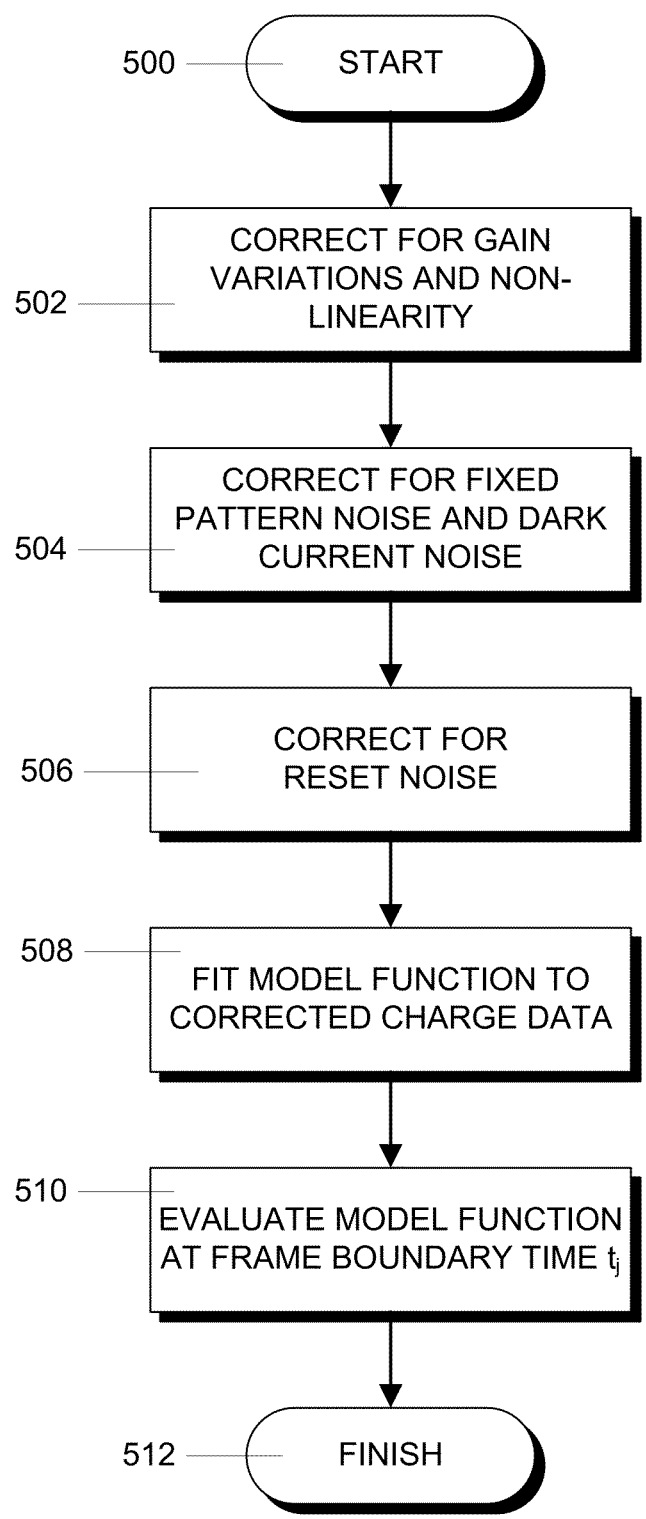
FIG. 5 is a flowchart showing the steps in an illustrative process for correcting for non-ideal sensor behavior.

In accordance with the principles of the invention, a process for calculating this estimate is shown in FIG. 5. The process begins in step 500 and proceeds to step 502 where the output of each pixel is corrected for differential gain and nonlinearity. Although each pixel in an ideal sensor would have a constant quantum gain g (the output of the pixel versus the input X-ray flux), in a real CMOS sensor, the response of each pixel is slightly different from the responses of other pixels. In particular, each pixel will have a slightly different linear quantum gain and the pixel output will also show a small nonlinearity. Both of these effects must be corrected before any other operations are carried out.

The correction is performed by measuring the output of each pixel in response to a large number (for example, 100) calibration images. Each calibration image is acquired with no object between the X-ray source and the X-ray sensor and with the X-ray shutter wide open (called a "flood field" image), but the images have different exposure times. The response of each pixel is then fitted to a curve of the form:

$$q_{lin,i}(t) = a_{0,i} + a_{1,i} q_{m,i}(t) + a_{2,i} q_{m,i}^2(t) + a_{3,i} q_{m,i}^3(t) + \ldots + a_{n,i} q_{m,i}^n(t) \quad (3)$$

where $q_{lin,i}$ is the corrected (linearized) charge in pixel i, $q_{m,i}$ is the measured charge in pixel i at time t and $a_0$ to $a_n$ are best fit coefficients determined by assuming that the pixel charge accumulates linearly with exposure time and adjusting the coefficients to produce the best linear approximation of the accumulated charge versus time. It has been found that, for CMOS sensors, a reasonably accurate linearization is obtained with n=3.

Next, in step 504, the pixel outputs are corrected for fixed pattern noise and dark current noise. The fixed pattern noise and dark current are also corrected via calibration. In this case, a series of identical dark calibration images (with the X-ray shutter closed) are acquired at an integration time of interest. For each pixel, the charge in each dark image is averaged over the set of identical dark calibration images and the resulting average charge for pixel i, $q_{dark,i}$, thus contains the both the fixed pattern noise, $n_{FPN}$, and the integrated dark current as given by:

$$q_{dark,i} = \int_{t_j}^{t_{j+1}} [i_{dark,i}] d\tau + n_{FPN,i} \quad (4)$$

Both of these noise contributions can then be removed from the linearized charge by subtracting $q_{dark,i}$ from the linearized charge.

Then, in step 506, reset noise is corrected. After each row of the CMOS X-ray sensor is read, the pixels in the row are reset to a reference voltage value. Ideally, pixels in each row would reset to the same reference voltage value. Reset noise occurs when the pixels in a row reset to a value slightly different from the reference voltage value by a random offset value. This noise appears as horizontal "striping" in the image because each pixel in a given row has the same random offset value. However, the random offset for each pixel row changes after each reset; consequently the reset noise cannot be corrected by calibration like dark current or fixed pattern noise. Therefore, reset noise must be estimated from each image by performing a frequency filtration on the image to determine the component with zero frequency in each row. In the process of this frequency filtration, bright signals (such as Bragg reflections) are detected and masked out. Then, a fast Fourier transform is applied to the image followed by low pass filtration. Alternatively, the reset noise can be estimated simply by masking off a number of pixels at the edge of the sensor and averaging the signal in these pixels. Either of these techniques gives the reset noise correction, $q_{reset,i}$ for a pixel i in a particular image.

After applying the above noise corrections the corrected charge $q_c$, for pixel i is given by:

$$q_{c,i}(t) = q_{lin,i}(t) - q_{dark,i}(t) - q_{reset,i} = \int_{t_j}^{t_{j+1}} [g(F_i(\tau) - F_i(t_j))] d\tau + n_{read,i} \quad (5)$$

Therefore, the integrated total X-ray flux at pixel i (neglecting read noise) is simply the sum of corrected charge in each pixel normalized by the average linear quantum conversion gain g:

$$F_{tot,i}(t) = \frac{1}{g} q_{c,i}(t) \quad (6)$$

In the next step, 508, an optimal estimate of the charge in each pixel at time $t_j$ (that is, at the read out time of frame j) is calculated given N measurements of the charge in that pixel during the frame integration time period. As discussed in detail in the methods described by Young above, this calculation is equivalent to fitting a low-order model function (with dimensionality much less than N) to the measured charges. However, the low-order model function cannot be a linear function (as was used by Young) because the X-ray intensity is not constant in time.

However, a higher-order function can be used. There are a number of possible basis functions. In particular, a cubic polynomial has been found to be a good fit to the rocking curve for most "fine sliced' data sets. This calculation reduces to the well known problem of minimizing $$\chi^2 = \Sigma (P_i(t) - q_{c,i}(t))^2 \quad (7)$$

where $P_i(t) = c_0 + c_1 t + c_2 t^2 + c_3 t^3 + \ldots + c_m t^m$ is a polynomial function of order m (where typically m=3) and $q_{c,i}(t)$ is a collection of charge measurements collected at N times during the frame integration time interval and corrected for noise as discussed above.

This equation can be solved for the optimal values of the polynomial coefficients by, for example, by the well-known technique of Singular Value Decomposition. If P is a good basis function for the measured charges, then the optimal fit will give a better estimate of the integrated charge in pixel i than a single measurement (by approximately the factor of $$\frac{1}{\sqrt{N}}$$

as long as N>>m).

Figure 6:
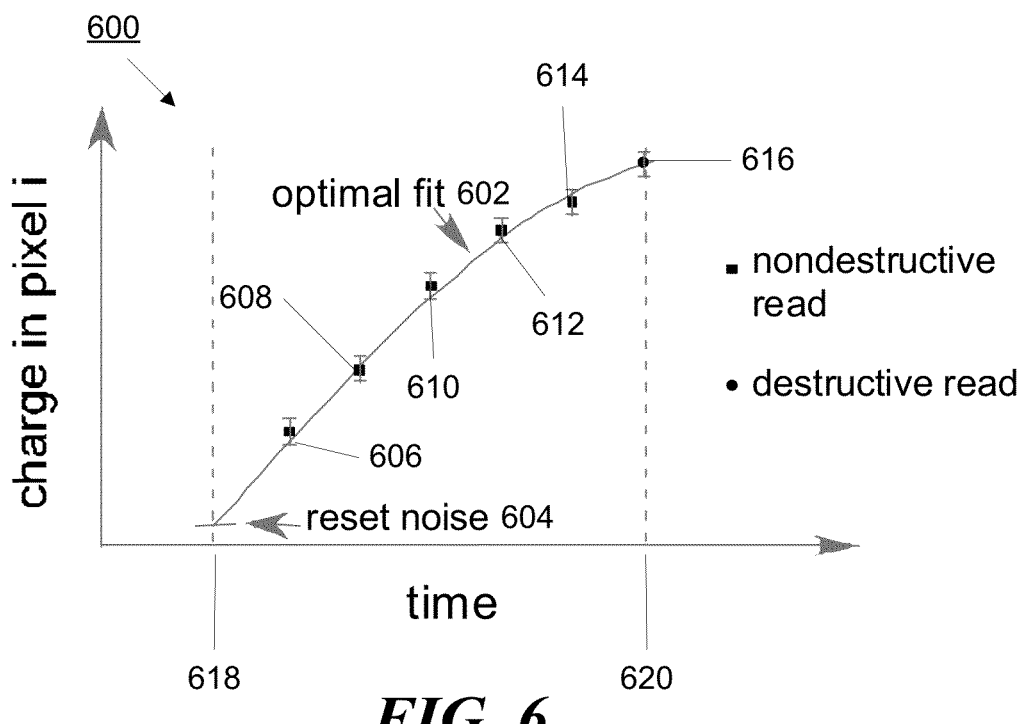
FIG. 6 is a graph of several samples of accumulated X-ray flux in a pixel with an optimal basis function fit to the samples.

The fitting process is illustrated in FIG. 6, which shows a graph of the accumulated pixel charge on the vertical axis versus time of the horizontal axis. As shown the charge increases non-linearly during the frame integration time starting at time 618 and ending at time 620. During the frame integration period, measurements 606-614 are taken of the accumulated charge by non-destructive reads. Each measurement includes an error-bar indicating the variance of the sample value. At the end of the frame integration period, the accumulated charge is reset to zero by a destructive read 616. The fitted basis curve is shown at 602.

By including an offset term $c_0$ in polynomial P, an allowance 604 can be made for a (presumably small) residual offset for each pixel in order to correct for the fact that the reset noise and/or fixed pattern noise corrections will not be perfect.

Finally, in step 510, the optimal estimate of the integrated X-ray fluence at pixel i can be obtained by evaluating the model function at the frame boundary, summing this over adjacent frames and then dividing by the conversion gain:

$$F_{tot,i} = \frac{1}{g} P(t_j) \qquad (8)$$

The process then finishes in step 512.

All of the corrections described above may, in principle, be carried out offline after data collection. However, offline processing significantly increases the data transmission load and also the data storage requirements. Therefore, a preferred embodiment implements the above procedure within the sensor hardware (employing either a field programmable gate array or a dedicated digital signal processor).

While the invention has been shown and described with reference to a number of embodiments thereof, it will be recognized by those skilled in the art that various changes in form and detail may be made herein without departing from the spirit and scope of the invention as defined by the appended claims.

What is claimed is:

1. A method for correcting pixel charge data for non-ideal behavior in a CMOS sensor of an X-ray diffraction system, comprising, for each pixel in the sensor:
   (a) non-destructively sampling charge accumulated in the pixel at a plurality of times during a sensor frame time period and correcting each sample value for gain variation and nonlinearity;
   (b) estimating fixed pattern and dark current noise for the pixel and subtracting the estimated fixed pattern and dark current noise from each corrected sample value;
   (c) estimating reset noise for the pixel and subtracting the estimated reset noise from each sample value corrected in step (b) to produce a plurality of corrected sample values;
   (d) fitting a model basis function of charge versus time to the corrected sample values produced in step (c); and
   (e) evaluating the fitted model basis function at an end time of the frame time period.

2. The method of claim 1 wherein step (a) comprises measuring the output of the pixel in response to a predetermined number of output calibration images produced by the sensor and fitting the pixel response to a model function of charge versus time.

3. The method of claim 2 wherein each output calibration image is a flood field image.

4. The method of claim 1 wherein step (b) comprises measuring the output of the pixel in response to a predetermined number of noise calibration images produced by the sensor and averaging the output of the pixel over the number of noise calibration images.

5. The method of claim 4 wherein the noise calibration images are identical dark images.

6. The method of claim 1 wherein step (c) comprises performing a spatial frequency filtration on an image produced by the sensor and containing the pixel to determine a component with zero spatial frequency in each row of the image and using the zero spatial frequency component as the estimated fixed pattern and dark current noise.

7. The method of claim 6 wherein the spatial frequency filtration comprises detecting and masking Bragg resonance signals and thereafter applying a fast Fourier transform to the image followed by low pass filtration.

8. The method of claim 1 wherein step (c) comprises averaging signals produced by a predetermined number of pixels, all of which are located at the edge of the sensor and using the average as the estimated fixed pattern and dark current noise.

9. The method of claim 1 wherein in step (d) the model basis function of charge versus time is a cubic polynomial of charge versus time.

10. The method of claim 1 further comprising summing the optimal estimate determined in step (e) over adjacent frame times and dividing the sum by the average conversion gain.

11. An X-ray diffraction system, comprising:
    an X-ray source;
    a CMOS sensor; and
    a pixel processing unit which, for each pixel in the sensor:
    (a) non-destructively samples charge accumulated in the pixel at a plurality of times during a sensor frame time period and corrects each sample value for gain variation and nonlinearity;
    (b) estimates fixed pattern and dark current noise for the pixel and subtracts the estimated fixed pattern and dark current noise from each corrected sample value;
    (c) estimates reset noise for the pixel and subtracts the estimated reset noise from each sample value corrected in step (b) to produce a plurality of corrected sample values;
    (d) fits a model basis function of charge versus time to the corrected sample values produced in step (c); and
    (e) evaluates the fitted model basis function at an end time of the frame time period.

12. The system of claim 11 wherein step (a) performed by the pixel processing unit comprises measuring the output of the pixel in response to a predetermined number of output calibration images produced by the sensor and fitting the pixel response to a model function of charge versus time.

13. The system of claim 12 wherein each output calibration image is a flood field image.

14. The system of claim 11 wherein step (b) performed by the pixel processing unit comprises measuring the output of the pixel in response to a predetermined number of noise calibration images produced by the sensor and averaging the output of the pixel over the number of noise calibration images.

15. The system of claim 14 wherein the noise calibration images are identical dark images.

16. The system of claim 11 wherein step (c) performed by the pixel processing unit comprises performing a spatial frequency filtration on an image produced by the sensor and containing the pixel to determine a component with zero spatial frequency in each row of the image and using the zero spatial frequency component as the estimated fixed pattern and dark current noise.

17. The system of claim 16 wherein the spatial frequency filtration comprises detecting and masking Bragg resonance signals and thereafter applying a fast Fourier transform to the image followed by low pass filtration.

18. The system of claim 11 wherein step (c) performed by the pixel processing unit comprises averaging signals produced by a predetermined number of pixels, all of which are located at the edge of the sensor and using the average as the estimated fixed pattern and dark current noise.

19. The system of claim 11 wherein in step (d) performed by the pixel processing unit, the model basis function of charge versus time is a cubic polynomial of charge versus time.

20. The system of claim 11 further comprising summing the optimal estimate determined in step (e) performed by the pixel processing unit over adjacent frame times and dividing the sum by the average conversion gain.

21. The system of claim 11 wherein the pixel processing unit comprises one of a fixed gate array and a digital signal processor which is integrated with readout electronics of the CMOS sensor.

22. The system of claim 11 wherein the pixel processing unit comprises a computer which receives pixel data from the CMOS sensor.

* * * * *